US011933619B2

(12) United States Patent
Marinescu et al.

(10) Patent No.: US 11,933,619 B2
(45) Date of Patent: Mar. 19, 2024

(54) SAFE ZONES AND ROUTES PLANNING

(71) Applicant: International Business Machines Corporation, Armonk, NY (US)

(72) Inventors: Radu Marinescu, Dublin (IE); Akihiro Kishimoto, Setagaya (JP)

(73) Assignee: International Business Machines Corporation, Armonk, NY (US)

( * ) Notice: Subject to any disclaimer, the term of this patent is extended or adjusted under 35 U.S.C. 154(b) by 555 days.

(21) Appl. No.: 17/114,168

(22) Filed: Dec. 7, 2020

(65) Prior Publication Data

US 2022/0178712 A1   Jun. 9, 2022

(51) Int. Cl.
G01C 21/34   (2006.01)
A61B 5/11    (2006.01)
G01S 19/01   (2010.01)

(52) U.S. Cl.
CPC ........ *G01C 21/3461* (2013.01); *A61B 5/1112* (2013.01); *G01S 19/01* (2013.01)

(58) Field of Classification Search
CPC .... G01C 21/3461; A61B 5/1112; G01S 19/01
See application file for complete search history.

(56) References Cited

U.S. PATENT DOCUMENTS

| | | | |
|---|---|---|---|
| 7,321,826 B2 | 1/2008 | Sheh et al. | |
| 8,583,365 B2 | 11/2013 | Jang et al. | |
| 8,866,608 B2 * | 10/2014 | Balinski | G16H 40/20 340/572.8 |
| 9,459,108 B2 | 10/2016 | Berlingerio et al. | |
| 9,541,412 B1 | 1/2017 | Botea et al. | |
| 10,012,514 B2 * | 7/2018 | Stenneth | G01C 21/3484 |
| 10,366,791 B1 * | 7/2019 | Thiagarajan | G16H 50/20 |

(Continued)

FOREIGN PATENT DOCUMENTS

| | | |
|---|---|---|
| CN | 110996067 A | 4/2020 |
| CN | 111261302 A | 6/2020 |

(Continued)

OTHER PUBLICATIONS

"Privacy-Preserving Cross-Border Contact Tracing", BlueTrace, Printed Nov. 2, 2020, 3 pages, <https://bluetrace.io/>.

(Continued)

*Primary Examiner* — Luis A Martinez Borrero
(74) *Attorney, Agent, or Firm* — Brandon L. Stephens; Sonny Z. Zhan

(57) ABSTRACT

In an approach for recommending a safe path for people to navigate an environment, a processor generates a contact graph for a user in a group of users in an area, based on a pre-defined distance measurement between the user and another user in a same timestamp during a pre-defined time period. A processor builds a profile for the user based on the contact graph, the profile including a probability model corresponding to the contact graph to estimate an infection probability for the user. A processor calculates an initial route for the user from a first location to a second location in the area. A processor analyzes an infection risk for the user based on the profile and other users within a pre-defined distance to the user in the initial route. A processor updates the initial route based on the analysis to minimize the risk to be infected.

20 Claims, 6 Drawing Sheets

(56) References Cited

U.S. PATENT DOCUMENTS

| | | | | |
|---|---|---|---|---|
| 10,520,327 | B2* | 12/2019 | Milbert | G01C 21/20 |
| 10,578,448 | B2* | 3/2020 | Ba | G01N 33/0031 |
| 11,011,277 | B1* | 5/2021 | Kelly | G06Q 50/22 |
| 11,164,269 | B1* | 11/2021 | Locke | H04W 4/024 |
| 11,333,512 | B2* | 5/2022 | Van Der Sluis | G08G 1/0129 |
| 11,397,861 | B2* | 7/2022 | Klasson | G06N 20/00 |
| 11,456,080 | B1* | 9/2022 | Jain | A61B 5/4815 |
| 11,504,011 | B1* | 11/2022 | Jain | G06N 5/04 |
| 11,586,825 | B2* | 2/2023 | Klasson | G06F 40/30 |
| 2007/0229290 | A1* | 10/2007 | Kahn | G16H 50/80 |
| | | | | 702/19 |
| 2011/0225046 | A1* | 9/2011 | Eldering | H04N 7/17318 |
| | | | | 705/14.53 |
| 2013/0138451 | A1* | 5/2013 | Shiono | G16H 50/80 |
| | | | | 705/2 |
| 2013/0226948 | A1 | 8/2013 | Ahn et al. | |
| 2013/0325979 | A1* | 12/2013 | Mansfield | H04W 4/029 |
| | | | | 709/206 |
| 2014/0067266 | A1 | 3/2014 | Berlingerio et al. | |
| 2014/0136226 | A1* | 5/2014 | Dittmer | G16Z 99/00 |
| | | | | 705/2 |
| 2015/0100330 | A1* | 4/2015 | Shpits | G16H 50/80 |
| | | | | 705/2 |
| 2016/0117937 | A1* | 4/2016 | Penders | G06F 16/9535 |
| | | | | 434/236 |
| 2016/0180060 | A1* | 6/2016 | Nelson | G06F 16/29 |
| | | | | 702/19 |
| 2017/0024531 | A1* | 1/2017 | Malaviya | G16H 50/30 |
| 2017/0039339 | A1* | 2/2017 | Bitran | G16H 50/30 |
| 2017/0209102 | A1* | 7/2017 | Parthasarathy | A61B 5/0059 |
| 2017/0316324 | A1* | 11/2017 | Barrett | G06N 20/20 |
| 2018/0052970 | A1* | 2/2018 | Boss | G06F 21/35 |
| 2018/0106629 | A1* | 4/2018 | Ishihara | G06T 17/00 |
| 2018/0106630 | A1* | 4/2018 | Otero Diaz | G01C 21/3484 |
| 2018/0245935 | A1* | 8/2018 | Ba | G01N 33/0031 |
| 2018/0308585 | A1* | 10/2018 | Holmes | G16H 50/70 |
| 2019/0098599 | A1* | 3/2019 | Dixon | G06N 5/04 |
| 2019/0182619 | A1* | 6/2019 | Dhanabalan | G01C 21/005 |
| 2019/0346274 | A1* | 11/2019 | Venkatraman | G01C 21/3446 |
| 2020/0004746 | A1* | 1/2020 | Randall | G06F 16/2455 |
| 2020/0134103 | A1* | 4/2020 | Mankovskii | G06F 40/56 |
| 2020/0244716 | A1* | 7/2020 | Mehta | G06Q 20/405 |
| 2020/0264000 | A1* | 8/2020 | Carrino | G01C 21/3461 |
| 2020/0335226 | A1* | 10/2020 | Hara | G01N 33/56983 |
| 2021/0073736 | A1* | 3/2021 | Alawi | G06Q 10/06315 |
| 2021/0084451 | A1* | 3/2021 | Williams | H04W 4/38 |
| 2021/0090750 | A1* | 3/2021 | Sadilek | G16H 50/30 |
| 2021/0125732 | A1* | 4/2021 | Patel | G06N 5/01 |
| 2021/0209055 | A1* | 7/2021 | Winston | G06F 8/314 |
| 2021/0215610 | A1* | 7/2021 | Robertson | G16H 10/40 |
| 2021/0215693 | A1* | 7/2021 | Amiel | G06N 3/02 |
| 2021/0216677 | A1* | 7/2021 | Santarone | G01S 3/48 |
| 2021/0280320 | A1* | 9/2021 | Arora | G16H 15/00 |
| 2021/0327595 | A1* | 10/2021 | Abdallah | A61B 5/02055 |
| 2022/0027565 | A1* | 1/2022 | Klasson | G16H 50/80 |
| 2022/0028557 | A1* | 1/2022 | Klasson | H04W 4/025 |
| 2022/0028561 | A1* | 1/2022 | Klasson | G06N 20/20 |
| 2022/0028562 | A1* | 1/2022 | Klasson | G06F 40/30 |
| 2022/0028563 | A1* | 1/2022 | Klasson | G16H 50/20 |
| 2022/0030382 | A1* | 1/2022 | Klasson | G16H 50/20 |
| 2022/0115137 | A1* | 4/2022 | Goldstein | G16H 10/60 |
| 2022/0136857 | A1* | 5/2022 | Pompili | G16H 50/70 |
| | | | | 701/409 |
| 2022/0170756 | A1* | 6/2022 | Imtiyaz Shaikh | H04W 4/44 |
| 2023/0007439 | A1* | 1/2023 | Williams | G06Q 10/0635 |
| 2023/0082658 | A1* | 3/2023 | Klasson | G16H 50/70 |
| | | | | 455/456.1 |

FOREIGN PATENT DOCUMENTS

| | | |
|---|---|---|
| IN | 202031006684 A | 3/2020 |
| JP | 6589125 B2 | 10/2019 |
| WO | 2014005979 A1 | 1/2014 |

OTHER PUBLICATIONS

"System and Method for Group Optimal Common Meeting Place Recommender using Individualized Spatio-Temporal Presence Information", An IP.com Prior Art Database Technical Disclosure, Disclosed Anonymously, IP.com No. 000220496, IP.com Electronic Publication: Aug. 2, 2012, 5 pages.

"Systems and Methods for a Smarter Metropolitan Transit Bus Recommender System", An IP.com Prior Art Database Technical Disclosure, Disclosed Anonymously, IP.com No. 000225758, IP.com Electronic Publication: Mar. 4, 2013, 8 pages.

Lones et al, "The Feasibility of an Infection Control "Safe Zone" in a Spinal Cord Injury", Infection Control And Hospital Epidemiology, vol. 37, No. 6, Jun. 2016, pp. 714-716.

Sainz, Fred, "Apple and Google partner on COVID-19 contact tracing technology", Apple, Apr. 10, 2020, 3 pages, <https://www.apple.com/newsroom/2020/04/apple-and-google-partner-on-covid-19-contact-tracing-technology/>.

* cited by examiner

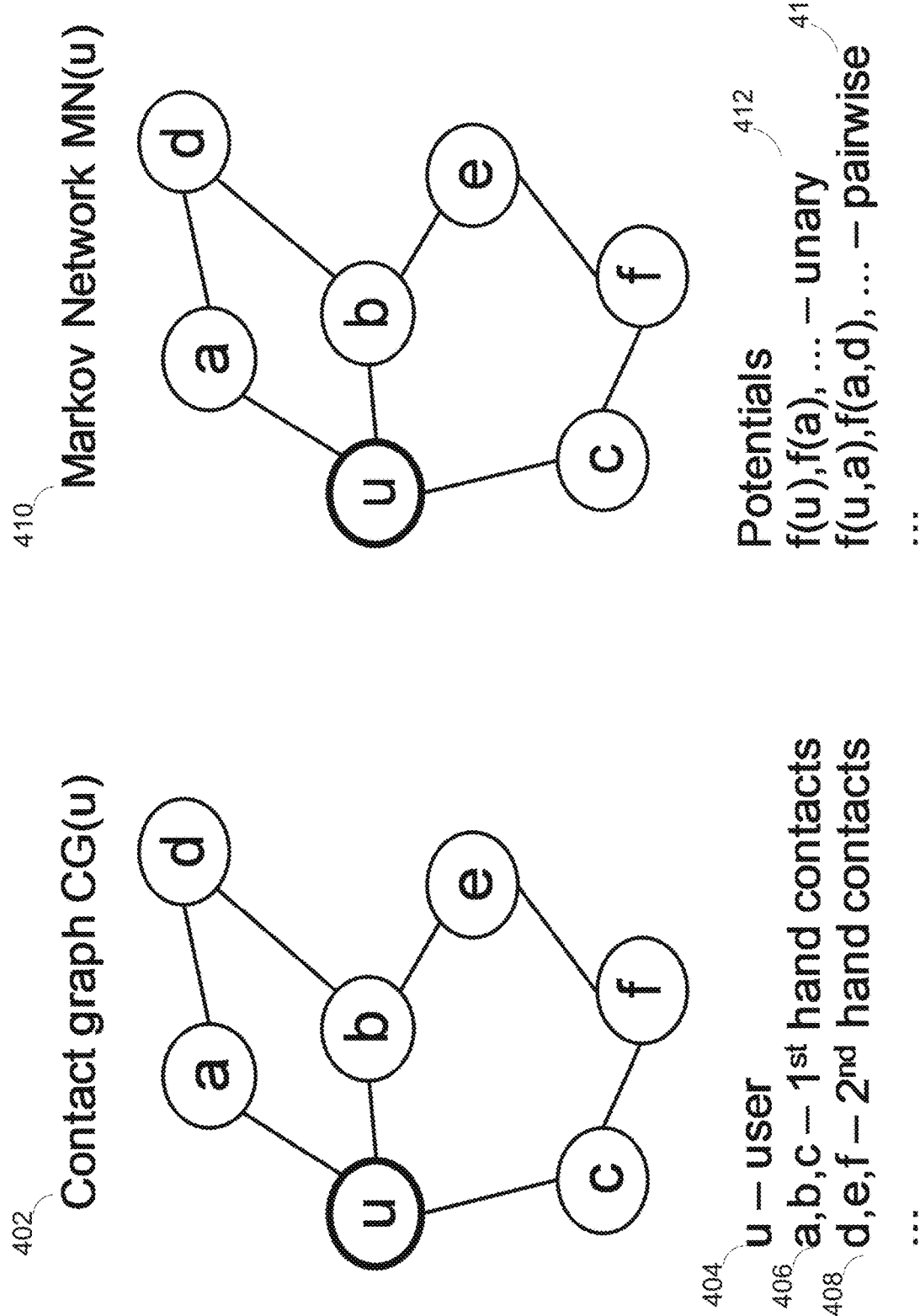

Dataset: N – not infected; Y - infected

| day | u | a | b | c | d | e | f |
|---|---|---|---|---|---|---|---|
| 1 | N | N | N | N | N | N | N |
| 2 | N | N | - | N | - | N | N |
| 3 | N | N | - | N | Y | - | Y |
| 4 | N | N | N | Y | Y | N | Y |
| ... | | | | | | | |

SAFE ZONES AND ROUTES PLANNING

BACKGROUND

The present disclosure relates generally to the field of data analysis, and more particularly to recommending a safe path for people to navigate an environment (indoors or outdoors) that minimizes a risk of getting contaminated or infected during a pandemic.

Across the world, governments and health authorities are working together to find solutions to a disease pandemic, to protect people and get society back up and running. Disease can be transmitted through close proximity to affected individuals. During a pandemic, a pathogen may be highly contagious and can even be transmitted via aerosols within a very short distance from an infected host. There may be limited public transport.

SUMMARY

Aspects of an embodiment of the present disclosure disclose an approach for recommending a safe path for people to navigate an environment. A processor generates a contact graph for a user in a group of users in an area, based on a pre-defined distance measurement between the user and another user in a same timestamp during a pre-defined time period. A processor builds a profile for the user based on the contact graph, the profile including a probability model corresponding to the contact graph to estimate an infection probability for the user. A processor calculates an initial route for the user from a first location to a second location in the area. A processor analyzes an infection risk for the user based on the profile and other users within a pre-defined distance to the user in the initial route. A processor updates the initial route based on the analysis to minimize the risk to be infected.

BRIEF DESCRIPTION OF THE DRAWINGS

FIGS. 4A-4C illustrate an exemplary function of building a user profile with the safe route planning module within the computing device of FIG. 1, in accordance with an embodiment of the present disclosure.

DETAILED DESCRIPTION

Figure 1:
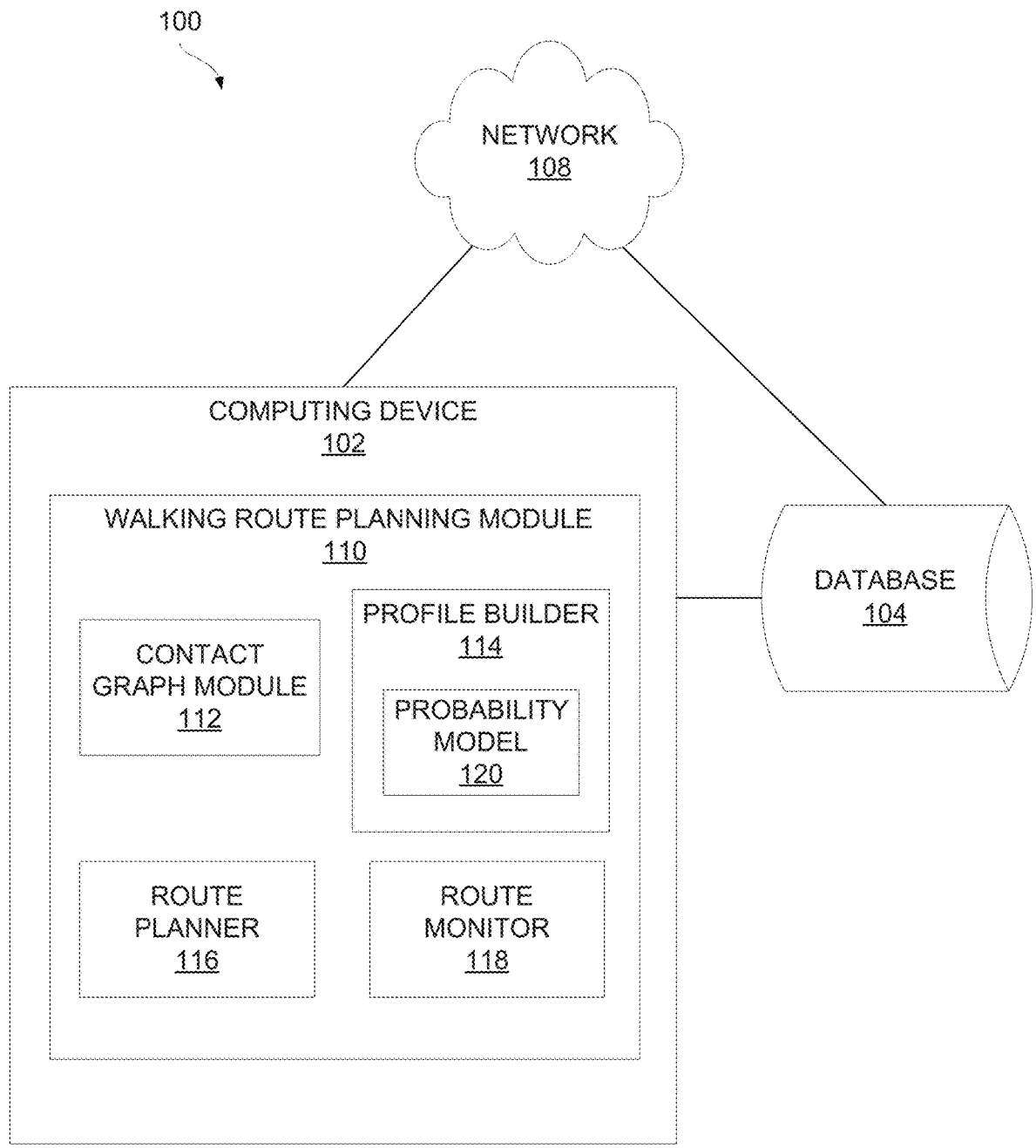
FIG. 1 is a functional block diagram illustrating a safe route planning environment, in accordance with an embodiment of the present disclosure.

The present disclosure is directed to systems and methods for recommending a safe path for people to navigate an environment (indoors or outdoors) that minimizes a risk of getting contaminated or infected during a pandemic.

Embodiments of the present disclosure recognize a need for minimizing the risk of getting contaminated during a pandemic. For example, in a pandemic or other health situation, the pathogen may be highly contagious and can even be transmitted via aerosols within a very short distance from an infected host. In this scenario, people may still need to go out of their home to get basic goods in order to survive. When doing so, people would like to navigate a safe route to the desired destination such that the risk of getting contaminated is minimized. For example, an individual may have to walk to a grocery store from the individual's home. The individual may need to follow a route that minimizes the risk of getting infected given that other people (some of which could be infected already) are traveling to the same destination or are likely to share segments of the individual's path. In another related scenario, embodiments of the present disclosure recognize a need for determining a safe route inside a store so that a shopper can go from the entrance to the destination while safely navigating the aisles to fulfil the shopping list while minimizing the risk of getting infected given that other, possibly infected shoppers, are also shopping in the same store. Embodiments of the present disclosure disclose analyzing the routes taken by the individuals and facilitating the task of tracking the cluster of infection area.

Embodiments of the present disclosure disclose collecting real-time information about the location of other people in an area (e.g., a neighborhood or public area) by, e.g., tracking phones used by people. Embodiments of the present disclosure disclose collecting real-time information about the medical history and building a profile for each of the active travelers. The profile may predict the likelihood of a person being infected as well as the infected area around the person. Embodiments of the present disclosure disclose calculating a route for a user to walk from an origin (e.g., home) to a destination (e.g., grocery store) that minimizes the risk of infection. Embodiments of the present disclosure disclose tracking the user's movement, as well as the movement of the other users (e.g., active travelers), and updating the route to reflect any change that might occur. Embodiments of the present disclosure disclose avoiding a high-risk zone that people with high probability of being infected are within a small distance of each other and people are close to a user's current position. Embodiments of the present disclosure disclose tracking and notifying a location of a potential unsafe zone according to the information on accumulated paths taken by all people in the area.

Embodiments of the present disclosure disclose automatically generating a safe route from a given origin to a destination that minimizes the risk of getting infected by a pathogen. Embodiments of the present disclosure disclose constantly monitoring the progress of the traveler and updating the route when other possibly high-risk travelers get close to the current traveler. Embodiments of the present disclosure disclose displaying safe zones on a map where the risk of getting infected is minimum. Embodiments of the present disclosure disclose building a probabilistic model using global position system (GPS) traces and medical records and using the model to compute the likelihood of a person being infected (i.e., posterior probability that an individual is infected). Embodiments of the present disclosure disclose building a probabilistic model using a group of volunteers willing to share their infected/not-infected status over a period of time. Embodiments of the present disclosure disclose using the number of close contacts (e.g., contact within less than six feet) as a proxy measure for the likelihood of infection. Embodiments of the present disclosure disclose inputting an origin and destination, GPS locations, census and medical information. Embodiments of the present disclosure disclose outputting a route from origin to destination that avoids contact with high-risk or infected persons. Embodiments of the present disclosure disclose a user interface that updates the information about an infected person. Embodiments of the present disclosure disclose analyzing one or more routes and identifying one or more people who share zones with infected persons. Embodiments of the present disclosure disclose providing safe routes in case of a pandemic to slow down the rate of infection. Embodiments of the present disclosure disclose calculating and recommending safe routes within a store such that a shopper avoids contact with possible high-risk or infected people that shop in the same store.

The present disclosure will now be described in detail with reference to the Figures. FIG. 1 is a functional block diagram illustrating a safe route planning environment, generally designated 100, in accordance with an embodiment of the present disclosure.

In the depicted embodiment, safe route planning environment 100 includes computing device 102, database 104, and network 108. In the depicted embodiment, database 104 is located externally and accessed through a communication network such as network 108 by computing device 102. Computing device 102 may access database 104 directly. In other embodiments, database 104 may be located on computing device 102. Database 104 may store available medical records. Database 104 may store real-time GPS tracking and map data and information. Database 104 may store real-time business transaction data. Database 104 may store monitored (e.g., camera circuited television) data.

In various embodiments of the present disclosure, computing device 102 can be a laptop computer, a tablet computer, a netbook computer, a personal computer (PC), a desktop computer, a mobile phone, a smartphone, a smart watch, a wearable computing device, a personal digital assistant (PDA), or a server. In another embodiment, computing device 102 represents a computing system utilizing clustered computers and components to act as a single pool of seamless resources. In other embodiments, computing device 102 may represent a server computing system utilizing multiple computers as a server system, such as in a cloud computing environment. In general, computing device 102 can be any computing device or a combination of devices with access to safe route planning module 110 and network 108 and is capable of processing program instructions and executing safe route planning module 110, in accordance with an embodiment of the present disclosure. Computing device 102 may include internal and external hardware components, as depicted and described in further detail with respect to FIG. 5.

Further, in the depicted embodiment, computing device 102 includes safe route planning module 110. In the depicted embodiment, safe route planning module 110 is located on computing device 102. However, in other embodiments, safe route planning module 110 may be located externally and accessed through a communication network such as network 108. The communication network can be, for example, a local area network (LAN), a wide area network (WAN) such as the Internet, or a combination of the two, and may include wired, wireless, fiber optic or any other connection known in the art. In general, the communication network can be any combination of connections and protocols that will support communications between computing device 102 and safe route planning module 110, in accordance with a desired embodiment of the disclosure.

In one or more embodiments, safe route planning module 110 is configured to generate a contact graph for a user in a group of users in an area, based on a pre-defined distance measurement between the user and another user in a same timestamp during a pre-defined time period. The user may be a traveler walking in the area where virus or other contagious disease may exist and can even be transmitted via aerosols within a very short distance from an infected host. In an example, the area can be a shopping store that the users do shopping inside the store. Safe route planning module 110 may generate the contact graph based on the pre-defined distance measurement between the user and another user at a same time in the area during a pre-defined time period. For example, the pre-defined distance can be six feet apart between the users. The pre-defined distance for measurement can be any other pre-defined distance. Safe route planning module 110 may measure a distance between the users using a global positioning system, for example, when each user may carry and use a mobile device receiving information from the global positioning system. In an example, the pre-defined time period can be a 14-days period or any other suitable time period. Safe route planning module 110 may collect real-time information about the location of other users in the area by tracking phones. Users can disable this feature or have to opt in to have their real-time information be obtained. Users are in control of what type of information is going to be collected and aware of how that information is going to be used. In an example, users are notified when the real-time information about the location is being collected. In another example, users can easily select or dis-allow the use of the user's GPS or real-time information.

Safe route planning module 110 may automatically detect of contacts, particularly regarding indirect contacts (e.g., contacting people who have not been infected yet but have a risk due to contact with infected people). Safe route planning module 110 may generate a contact graph based on GPS data relating to the group of users in an area. GPS data can be a set of timestamped traces of mobile devices over time period for the group of users. GPS data can be stored and accessed from database 104. In an example, safe route planning module 110 may trace the group of users using GPS data for a time period. Safe route planning module 110 may add a user pair to the contact graph when safe route planning module 110 determines that the distance between the user pair is smaller than a pre-defined threshold, e.g., six feet or any other suitable distance, with the same timestamps of the user pair in the area. In another example, safe route planning module 110 may look for two sets of locations that have the same position and consecutive timestamps which correspond to two users that have not changed positions for some time and therefore are in direct contact. In another example, safe route planning module 110 may use time-stamped business (e.g. credit card) transactions or even timestamped/geolocated camera monitored data (e.g., close circuit television monitored data) to identify possible close contacts between the group of users. Users can disable this feature or have to opt in to have their real-time information be obtained. Users are in control of what type of information is going to be collected and aware of how that information is going to be used. In an example, users are notified when the real-time information about the location is being collected. In another example, users can easily select or dis-allow the use of the user's business transaction, monitored real time or any other user information. An example contact graph is further depicted and described in further detail with respect to FIG. 4A.

In one or more embodiments, safe route planning module 110 is configured to build a profile for a user based on the contact graph. The profile may include probability model 120 corresponding to the contact graph to estimate an infection probability for the user. Safe route planning module 110 may use probabilistic model 120 to estimate the infection status of the user given possible infections of other users in the user's contact graph. In an example, probability model 120 may be a Markov network with a same structure based on the contact graph. The profile may predict the likelihood of the user being infected as well as the infected area around the user. Safe route planning module 110 may generate a dataset based on position data collected from a GPS and medical data available from the group of users. Safe route planning module 110 may collect real-time information about the medical history and may build the profile for each of the user. Users can disable this feature or have to opt in to have their real-time information be obtained. Users are in control of what type of information is going to be collected and aware of how that information is going to be used. In an example, users are notified when the real-time information is being collected. In another example, users can easily select or dis-allow the use of the user's business transaction, monitored real time data or any other user information. For each user, safe route planning module 110 may use available medical data and GPS location history for the past certain time (e.g., 14 days) to determine infected/non-infected state for each user in the contact graph of each user. For example, in day 12, users A and B may be located within a certain distance (e.g., within 6 feet). If user A is infected (based on the available medical data), safe route planning module 110 may determine that user B will likely be infected in the same day with some probability greater than 0. An example profile (e.g., Markov network) is further depicted and described in further detail with respect to FIGS. 4B-4C.

In an example, safe route planning module 110 may build probabilistic model 120 using GPS traces and available medical records to compute the likelihood of an individual being infected (i.e., posterior probability that an individual is infected). Safe route planning module 110 may build probabilistic model 120 using information from a group of volunteers willing to share their infected/not-infected status over a time period. In another example, safe route planning module 110 may use the number of close contacts (e.g., contacts within less than a certain distance, e.g., 6 feet) as a proxy measure for the likelihood of infection. Safe route planning module 110 may determine that the larger the number of close contacts a user has over a certain period (e.g., 14 days) the more likely the user is to be infected. Safe route planning module 110 may determine that the user's prior probability may be larger than that of the users with relatively few close contacts. Safe route planning module 110 may determine that a user in close contact with another infected user may be infected with a given large probability. Each user may have a small prior probability of being infected which will also account for the asymptomatic users.

In one or more embodiments, safe route planning module 110 is configured to calculate an initial route for the user from a first location (e.g., origin) to a second location (e.g., destination) in a certain area. In an example, the certain area can be in a walking area. In another example, the certain area can be a shopping store or other walking place. Safe route planning module 110 may calculate the initial route using an algorithm to calculate and generate the shortest route as the initial route. Safe route planning module 110 may calculate a route that minimizes the risk of infection. Safe route planning module 110 may track the user's movement, as well as the movement of the other active users (e.g., travelers in the same area). Safe route planning module 110 may update the route to reflect any change that might occur. Safe route planning module 110 may provide a recommendation to avoid a high-risk zone that appears because more people with high probability of being infected are within a small distance of each other and people are close to the user's current position. Safe route planning module 110 may track and notify a location of a potential unsafe zone according to the information on accumulated paths taken by all people (e.g., all users in the area).

In one or more embodiments, safe route planning module 110 is configured to analyze an infection risk for the user based on the profile and other users within a pre-defined distance to the user in the initial route. Safe route planning module 110 may analyze the infection risk for the user based on the profile and other users within a pre-defined distance to the user in the initial route. Safe route planning module 110 may analyze the infection risk for the user by analyzing multiple routes within the area and identifying users who share zones with other infected users. Safe route planning module 110 may automatically generate a safe route from a given origin to a destination that minimizes the risk of getting infected by a pathogen. Safe route planning module 110 may monitor the progress of the user (e.g., traveler) and may update the route when other possibly high-risk users (e.g., travelers) get close to the current traveler. Safe route planning module 110 may display safe zones on a map where the risk of getting infected is minimum.

In an example, safe route planning module 110 may take as input an origin and destination, GPS locations, and census and medical information of a group of users in the area. Safe route planning module 110 may output a route from origin to destination that avoids contact with high-risk or infected persons. For example, safe route planning module 110 may find a close user u' to origin O. If the probability P(u'=infected) is greater than a threshold and location(u') is less than a certain distance (e.g., six feet) from the initial route, safe route planning module 110 may mark u' as possible risk. Safe route planning module 110 may generate a Markov network (denoting as MN(u')) to estimate the marginal P(u'=infected). Safe route planning module 110 may use a standard inference algorithm such as variable elimination. Safe route planning module 110 may find a location (x,y) that is at least the certain distance apart (e.g., 6 feet) from u' location and reroute the initial route R0 to go through the safer location (x,y). Safe route planning module 110 may determine a shortest-path with the constraint that (x,y) must belong to the route.

In one or more embodiments, safe route planning module 110 is configured to dynamically update the initial route based on the analysis to minimize the risk for the user to be infected. Safe route planning module 110 may track the user's movement, as well as the movement of the other active travelers. Safe route planning module 110 may update the initial route to reflect any changes that might occur. For example, safe route planning module 110 may update the initial route to avoid a high-risk zone that appears more people with high probability of being infected are within a small distance of each other and are close to the user's current position. Safe route planning module 110 may track and notify a location of a potential unsafe zone according to the information on accumulated routes taken by all users traveling in the area. Safe route planning module 110 may provide a user interface to update the information about an infected person. Safe route planning module 110 may analyze one or more routes to identify people who share zones with an infected person.

In the depicted embodiment, safe route planning module 110 includes contact graph module 112, profile builder 114, route planner 116 and route monitor 118. In one or more embodiments, contact graph module 112 is configured to generate a contact graph for a user in a group of users in an area, based on a pre-defined distance measurement between the user and another user in a same timestamp during a pre-defined time period. The user may be a traveler walking in the area where virus or other contagious disease may exist and can even be transmitted via aerosols within a very short distance from an infected host. In an example, the area can be a shopping store that the users do shopping inside the store. Contact graph module 112 may generate the contact graph based on the pre-defined distance measurement between the user and another user at a same time in the area during a pre-defined time period. For example, the pre-defined distance can be six feet apart between the users. The pre-defined distance for measurement can be any other pre-defined distance. Contact graph module 112 may perform measurement of a distance between the users using a global positioning system, for example, when each user may carry and use a mobile device receiving information from the global positioning system. In an example, the pre-defined time period can be a 14-days period or any other suitable time period. Contact graph module 112 may collect real-time information about the location of other users in the area by tracking phones. Users can disable this feature or have to opt in to have their real-time information be obtained. Users are in control of what type of information is going to be collected and aware of how that information is going to be used. In an example, users are notified when the real-time information about the location is being collected. In another example, users can easily select or dis-allow the use of the user's GPS or real-time information.

Contact graph module 112 may automatically detect of contacts, particularly regarding indirect contacts (e.g., contacting people who have not been infected yet but have a risk due to contact with infected people). Contact graph module 112 may generate a contact graph based on GPS data relating to the group of users in an area. GPS data can be a set of timestamped traces of mobile devices over time period for the group of users. GPS data can be stored and accessed from database 104. In an example, contact graph module 112 may trace the group of users using GPS data for a time period. Contact graph module 112 may add a user pair to the contact graph when safe route planning module 110 determines that the distance between the user pair is smaller than a pre-defined threshold, e.g., six feet or any other suitable distance, with the same timestamps of the user pair in the area. In another example, contact graph module 112 may look for two sets of locations that have the same position and consecutive timestamps which correspond to two users that have not changed positions for some time and therefore are in direct contact. In another example, contact graph module 112 may use timestamped business (e.g. credit card) transactions or even timestamped/geolocated camera monitored data (e.g., close circuit television monitored data) to identify possible close contacts between the group of users. Users can disable this feature or have to opt in to have their real-time information be obtained. Users are in control of what type of information is going to be collected and aware of how that information is going to be used. In an example, users are notified when the real-time information about the location is being collected. In another example, users can easily select or dis-allow the use of the user's business transaction, monitored real time or any other user information. An example contact graph is further depicted and described in further detail with respect to FIG. 4A.

In one or more embodiments, profile builder 114 is configured to build a profile for a user based on a contact graph. In the depicted embodiment, profile builder 114 includes probability model 120 corresponding to the contact graph to estimate an infection probability for the user. Probabilistic model 120 may estimate the infection status of the user given possible infections of other users in the user's contact graph. In an example, probability model 120 may be a Markov network with a same structure based on the contact graph. The profile may predict the likelihood of the user being infected as well as the infected area around the user. Profile builder 114 may generate a dataset based on position data collected from a GPS and medical data available from the group of users. Profile builder 114 may collect real-time information about the medical history and may build the profile for each of the user. Users can disable this feature or have to opt in to have their real-time information be obtained. Users are in control of what type of information is going to be collected and aware of how that information is going to be used. In an example, users are notified when the real-time information is being collected. In another example, users can easily select or dis-allow the use of the user's medical history, business transaction, monitored real time data or any other user information. For each user, profile builder 114 may use available medical data and GPS location history for the past certain time (e.g., 14 days) to determine infected/non-infected state for each user in the contact graph of each user. For example, in day 12, users A and B may be located within a certain distance (e.g., within 6 feet). If user A is infected (based on the available medical data), safe route planning module 110 may determine that user B will likely be infected in the same day with some probability greater than 0. An example profile (e.g., Markov network) is further depicted and described in further detail with respect to FIGS. 4B-4C.

In an example, profile builder 114 may build probabilistic model 120 using GPS traces and available medical records to compute the likelihood of an individual being infected (i.e., posterior probability that an individual is infected). Profile builder 114 may build probabilistic model 120 using information from a group of volunteers willing to share their infected/not-infected status over a time period. In another example, profile builder 114 may use the number of close contacts (e.g., contacts within less than a certain distance, e.g., 6 feet) as a proxy measure for the likelihood of infection. Profile builder 114 may determine that the larger the number of close contacts a user has over a certain period (e.g., 14 days) the more likely the user is to be infected. Profile builder 114 may determine that the user's prior probability may be larger than that of the users with relatively few close contacts. Profile builder 114 may determine that a user in close contact with another infected user may be infected with a given large probability.

In one or more embodiments, route planner 116 is configured to calculate an initial route for the user from a first location (e.g., origin) to a second location (e.g., destination) in a certain area. In an example, the certain area can be in a walking area. In another example, the certain area can be a shopping store or other walking place. Route planner 116 may calculate the initial route using an algorithm to calculate and generate the shortest route as the initial route. Route planner 116 may calculate a route that minimizes the risk of infection. Route planner 116 may provide a recommendation to avoid a high-risk zone that appears because more people with high probability of being infected are within a small distance of each other and people are close to the user's current position. Route planner 116 may track and notify a location of a potential unsafe zone according to the information on accumulated paths taken by all people (e.g., all users in the area).

In one or more embodiments, route planner 116 is configured to analyze an infection risk for the user based on the profile and other users within a pre-defined distance to the user in the initial route. Route planner 116 may analyze the infection risk for the user based on the profile and other users within a pre-defined distance to the user in the initial route. Route planner 116 may analyze the infection risk for the user by analyzing multiple routes within the area and identifying users who share zones with other infected users. Route planner 116 may automatically generate a safe route from a given origin to a destination that minimizes the risk of getting infected by a pathogen. In an example, route planner 116 may take as input an origin and destination, GPS locations, and census and medical information of a group of users in the area. Route planner 116 may output a route from origin to destination that avoids contact with high-risk or infected persons. For example, route planner 116 110 may find a close user u' to origin O. If the probability P(u'=infected) is greater than a threshold and location(u') is less than a certain distance (e.g., six feet) from the initial route, route planner 116 may mark u' as possible risk. Route planner 116 may generate a Markov network (denoting as MN(u')) to estimate the marginal P(u'=infected). Safe route planning module 110 may use a standard inference algorithm such as variable elimination. Route planner 116 may find a location (x,y) that is at least the certain distance apart (e.g., 6 feet) from u' location and reroute the initial route R0 to go through the safer location (x,y). Route planner 116 may determine a shortest-path with the constraint that (x,y) must belong to the route.

In one or more embodiments, route monitor 118 is configured to dynamically update the initial route based on the analysis to minimize the risk for the user to be infected. Route monitor 118 may monitor the progress of the user (e.g., traveler) and may update the route when other possibly high-risk users (e.g., travelers) get close to the current traveler. Route monitor 118 may display safe zones on a map where the risk of getting infected is minimum. Route monitor 118 may track the user's movement, as well as the movement of the other active travelers. Route monitor 118 may update the initial route to reflect any changes that might occur. For example, route monitor 118 may update the initial route to avoid a high-risk zone that appears more people with high probability of being infected are within a small distance of each other and are close to the user's current position. Route monitor 118 may track and notify a location of a potential unsafe zone according to the information on accumulated routes taken by all users traveling in the area. Route monitor 118 may provide a user interface to update the information about an infected person. Route monitor 118 may analyze one or more routes to identify people who share zones with an infected person.

Figure 2:
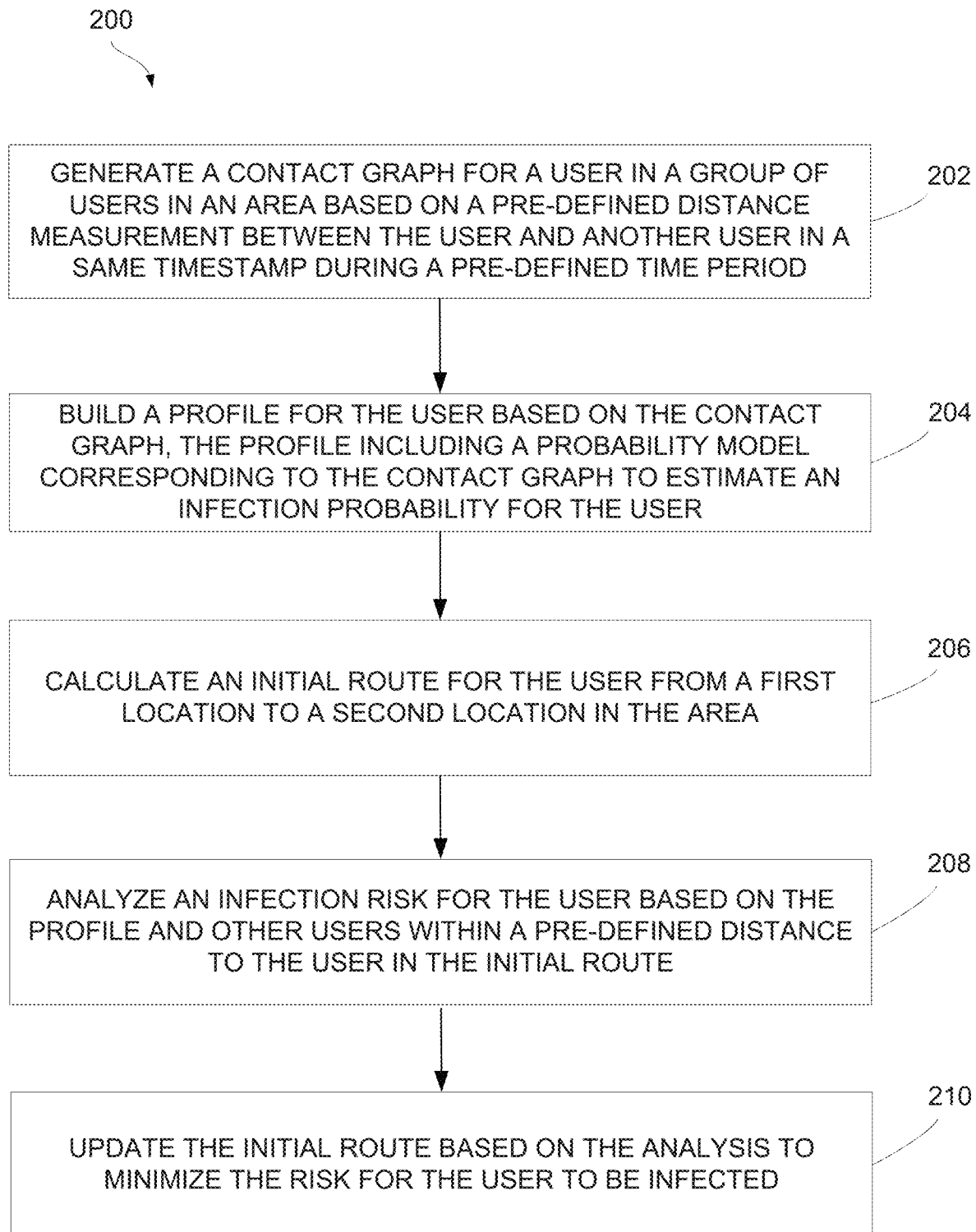
FIG. 2 is a flowchart depicting operational steps of a safe route planning module within a computing device of FIG. 1, in accordance with an embodiment of the present disclosure.

FIG. 2 is a flowchart 200 depicting operational steps of safe route planning module 110 in accordance with an embodiment of the present disclosure.

Safe route planning module 110 operates to generate a contact graph for a user in a group of users in an area, based on a pre-defined distance measurement between the user and another user in a same timestamp during a pre-defined time period. Safe route planning module 110 also operates to builds a profile for a user based on the contact graph. The profile may include probability model 120 corresponding to the contact graph to estimate an infection probability for the user. Safe route planning module 110 operates to calculate an initial route for the user from a first location to a second location in the certain area. Safe route planning module 110 operates to analyze an infection risk for the user based on the profile and other users within a pre-defined distance to the user in the initial route. Safe route planning module 110 operates to update the initial route based on the analysis to minimize the risk to be infected.

In step 202, safe route planning module 110 generate a contact graph for a user in a group of users in an area, based on a pre-defined distance measurement between the user and another user in a same timestamp during a pre-defined time period. The user may be a traveler walking in the area where virus or other contagious disease may exist and can even be transmitted via aerosols within a very short distance from an infected host. In an example, the area can be a shopping store that the users do shopping inside the store. Safe route planning module 110 may generate the contact graph based on the pre-defined distance measurement between the user and another user at a same time in the area during a pre-defined time period. For example, the pre-defined distance can be six feet apart between the users. The pre-defined distance for measurement can be any other pre-defined distance. Safe route planning module 110 may measure a distance between the users using a global positioning system, for example, when each user may carry and use a mobile device receiving information from the global positioning system. In an example, the pre-defined time period can be a 14-days period or any other suitable time period. Safe route planning module 110 may collect real-time information about the location of other users in the area by tracking phones. Users can disable this feature or have to opt in to have their real-time information be obtained. Users are in control of what type of information is going to be collected and aware of how that information is going to be used. In an example, users are notified when the real-time information about the location is being collected. In another example, users can easily select or dis-allow the use of the user's GPS or real-time information.

Safe route planning module 110 may automatically detect of contacts, particularly regarding indirect contacts (e.g., contacting people who have not been infected yet but who have a risk due to contact with infected people). Safe route planning module 110 may generate a contact graph based on GPS data relating to the group of users in an area. GPS data can be a set of timestamped traces of mobile devices over time period for the group of users. GPS data can be stored and accessed from database 104. In an example, safe route planning module 110 may trace the group of users using GPS data for a time period. Safe route planning module 110 may add a user pair to the contact graph when safe route planning module 110 determines that the distance between the user pair is smaller than a pre-defined threshold, e.g., six feet or any other suitable distance, with the same timestamps of the user pair in the area. In another example, safe route planning module 110 may look for two sets of locations that have the same position and consecutive timestamps which correspond to two users that have not changed positions for some time and therefore are in direct contact. In another example, safe route planning module 110 may use time-stamped business (e.g. credit card) transactions or even timestamped/geolocated camera monitored data (e.g., close circuit television monitored data) to identify possible close contacts between the group of users. Users can disable this feature or have to opt in to have their real-time information be obtained. Users are in control of what type of information is going to be collected and aware of how that information is going to be used. In an example, users are notified when the real-time information about the location is being collected. In another example, users can easily select or disallow the use of the user's business transaction, monitored real time or any other user information. An example contact graph is further depicted and described in further detail with respect to FIG. 4A.

In step 204, safe route planning module 110 builds a profile for a user based on the contact graph. The profile may include probability model 120 corresponding to the contact graph to estimate an infection probability for the user. Safe route planning module 110 may use probabilistic model 120 to estimate the infection status of the user given possible infections of other users in the user's contact graph. In an example, probability model 120 may be a Markov network with a same structure based on the contact graph. The profile may predict the likelihood of the user being infected as well as the infected area around the user. Safe route planning module 110 may generate a dataset based on position data collected from a GPS and medical data available from the group of users. Safe route planning module 110 may collect real-time information about the medical history and may build the profile for each of the user. Users can disable this feature or have to opt in to have their real-time information be obtained. Users are in control of what type of information is going to be collected and aware of how that information is going to be used. In an example, users are notified when the real-time information is being collected. In another example, users can easily select or dis-allow the use of the user's business transaction, monitored real time data or any other user information. For each user, safe route planning module 110 may use available medical data and GPS location history for the past certain time (e.g., 14 days) to determine infected/non-infected state for each user in the contact graph of each user. For example, in day 12, users A and B may be located within a certain distance (e.g., within 6 feet). If user A is infected (based on the available medical data), safe route planning module 110 may determine that user B will likely be infected in the same day with some probability greater than 0. An example profile (e.g., Markov network) is further depicted and described in further detail with respect to FIGS. 4B-4C.

In an example, safe route planning module 110 may build probabilistic model 120 using GPS traces and available medical records to compute the likelihood of an individual being infected (i.e., posterior probability that an individual is infected). Safe route planning module 110 may build probabilistic model 120 using information from a group of volunteers willing to share their infected/not-infected status over a time period. In another example, safe route planning module 110 may use the number of close contacts (e.g., contacts within less than a certain distance, e.g., 6 feet) as a proxy measure for the likelihood of infection. Safe route planning module 110 may determine that the larger the number of close contacts a user has over a certain period (e.g., 14 days) the more likely the user is to be infected. Safe route planning module 110 may determine that the user's prior probability may be larger than that of the users with relatively few close contacts. Safe route planning module 110 may determine that a user in close contact with another infected user may be infected with a given large probability. Each user may have a small prior probability of being infected which will also account for the asymptomatic users.

In step 206, safe route planning module 110 calculates an initial route for the user from a first location (e.g., origin) to a second location (e.g., destination) in a certain area. In an example, the certain area can be in a walking area. In another example, the certain area can be a shopping store or other walking place. Safe route planning module 110 may calculate the initial route using an algorithm to calculate and generate the shortest route as the initial route. Safe route planning module 110 may calculate a route that minimizes the risk of infection. Safe route planning module 110 may track the user's movement, as well as the movement of the other active users (e.g., travelers in the same area). Safe route planning module 110 may update the route to reflect any change that might occur. Safe route planning module 110 may provide a recommendation to avoid a high-risk zone that appears because more people with high probability of being infected are within a small distance of each other and people are close to the user's current position. Safe route planning module 110 may track and notify a location of a potential unsafe zone according to the information on accumulated paths taken by all people (e.g., all users in the area).

In step 208, safe route planning module 110 analyzes an infection risk for the user based on the profile and other users within a pre-defined distance to the user in the initial route. Safe route planning module 110 may analyze the infection risk for the user based on the profile and other users within a pre-defined distance to the user in the initial route. Safe route planning module 110 may analyze the infection risk for the user by analyzing multiple routes within the area and identifying users who share zones with other infected users. Safe route planning module 110 may automatically generate a safe route from a given origin to a destination that minimizes the risk of getting infected by a pathogen. Safe route planning module 110 may monitor the progress of the user (e.g., traveler) and may update the route when other possibly high-risk users (e.g., travelers) get close to the current traveler. Safe route planning module 110 may display safe zones on a map where the risk of getting infected is minimum.

In an example, safe route planning module 110 may take as input an origin and destination, GPS locations, and census and medical information of a group of users in the area. Safe route planning module 110 may output a route from origin to destination that avoids contact with high-risk or infected persons. For example, safe route planning module 110 may find a close user u' to origin O. If the probability P(u'=infected) is greater than a threshold and location (u') is less than a certain distance (e.g., six feet) from the initial route, safe route planning module 110 may mark u' as possible risk. Safe route planning module 110 may generate a Markov network (denoting as MN(u')) to estimate the marginal P(u'=infected). Safe route planning module 110 may use a standard inference algorithm such as variable elimination. Safe route planning module 110 may find a location (x,y) that is at least the certain distance apart (e.g., 6 feet) from u' location and reroute the initial route R0 to go through the safer location (x,y). Safe route planning module 110 may determine a shortest-path with the constraint that (x,y) must belong to the route.

In step 210, safe route planning module 110 updates the initial route based on the analysis to minimize the risk for the user to be infected. Safe route planning module 110 may track the user's movement, as well as the movement of the other active travelers. Safe route planning module 110 may update the initial route to reflect any changes that might occur. For example, safe route planning module 110 may update the initial route to avoid a high-risk zone that appears more people with high probability of being infected are within a small distance of each other and are close to the user's current position. Safe route planning module 110 may track and notify a location of a potential unsafe zone according to the information on accumulated routes taken by all users traveling in the area. Safe route planning module 110 may provide a user interface to update the information about an infected person. Safe route planning module 110 may analyze one or more routes to identify people who share zones with an infected person.

Figure 3:
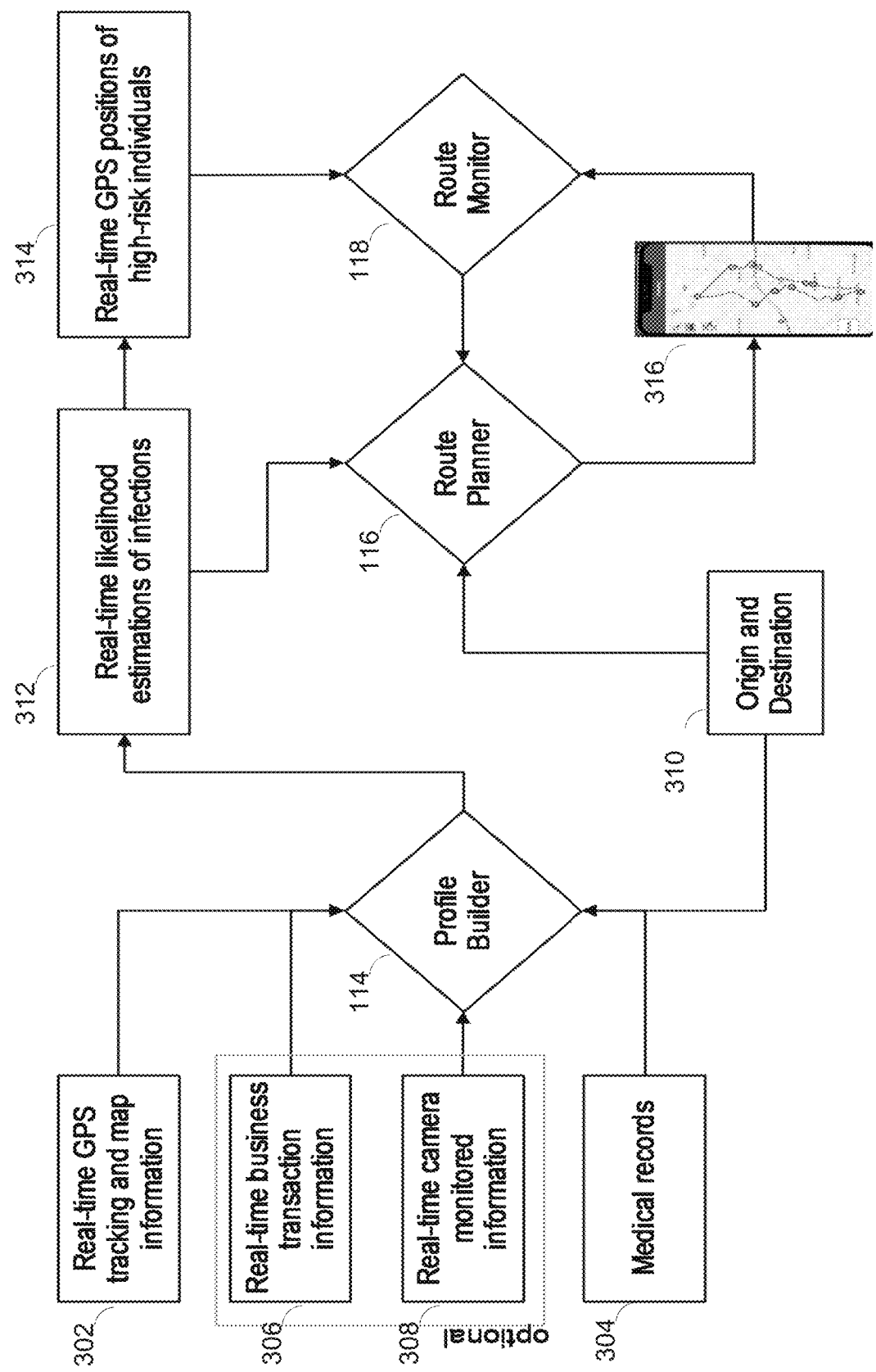
FIG. 3 illustrates an exemplary functional diagram of the safe route planning module within the computing device of FIG. 1, in accordance with an embodiment of the present disclosure.

FIG. 3 illustrates an exemplary functional diagram of safe route planning module 110 in accordance with one or more embodiments of the present disclosure.

In the example of FIG. 3, safe route planning module 110 may take as input origin and destination 310, real-time GPS tracking and map information 302, medical records 304, real-time business transaction information 306, and real-time camera monitored information 308 in an area. Profile builder 114 may build a profile for a user based on a contact graph based on the inputs. Profile builder 114 may provide real-time likelihood estimation of infections 312. Profile builder 114 may estimate the infection status of the user given possible infections of other users in the user's contact graph. Route planner 116 may receive information of origin and destination 310 and real-time likelihood estimation of infections 312. Route planner 116 may calculate an initial route for the user from the origin the destination. Route planner 116 may calculate the initial route using an algorithm to calculate and generate the shortest route as the initial route. Route planner 116 may calculate a route that minimizes the risk of infection. Route planner 116 may recommend and output a route in user interface 316 for a user to avoid a high-risk zone. Route planner 116 may output in user interface 316 a route from origin to destination that avoids contact with high-risk or infected persons. Route planner 116 may dynamically update the initial route based on the analysis to minimize the risk for the user to be infected. Route monitor 118 may monitor the progress of the user (e.g., traveler) by information of real-time GPS position of high-risk individuals 314. Route monitor 118 may send updated information to route planner 116 to dynamically update the route to minimize the risk for the user. Route monitor 118 may track the user's movement, as well as the movement of the other active travelers.

FIGS. 4A-4C illustrate an exemplary function of building a user profile of safe route planning module 110 in accordance with one or more embodiments of the present disclosure.

In the example of FIG. 4A, contact graph 402 includes user u 404. Contacts (a, b, c) 406 are first hand contacts of user u 402. A first hand contact may be a contact that a user has been in a pre-defined distance with, at the same time during a pre-defined time period. For example, the pre-defined distance can be within six feet between the users. The pre-defined distance for measurement can be any other pre-defined distance. Safe route planning module 110 may measure a distance between the users using a global positioning system, for example, when each user may carry and use a mobile device receiving information from the global positioning system. In an example, the pre-defined time period can be a 14-days period or any other suitable time period. Contacts (d, e, f) 408 are second hand contacts of user u 402 as contacts (d, e, f) 408 are first hand contacts of contacts (a, b, c) 406 respectively.

In the example of FIGS. 4B, safe route planning module 110 may build a user profile for a user based on contact graph 402. The user profile includes Markov network 410 with a same structure based on contact graph 402. Markov network 410 may predict the likelihood of the user being infected as well as the infected area around the user. For example, intuitively, unary potentials f(x) 412 may model the prior likelihood that contact x is infected. Similarly, pairwise potentials f(x,y) 414 may model the interaction between two persons, possibly infected. If both x and y are infected than f(x,y) has a large value. If x and y are not infected, then f(x,y) should be a small value. If either one is infected, then f(x,y) should have a moderate value. In an example, Markov network 410 may learn the potentials from medical records over a certain time period, e.g., 14 days. As shown in the example of FIG. 4C, safe route planning module 110 may generate dataset 416, for example, using available medical records from users over a certain time period, e.g., last 14 days. Safe route planning module 110 may leverage GPS location data to infer that if x and y are located within less than a certain distance (e.g., six feet) from each other and if x is infected then with a probability over a threshold (e.g., 0.7), Markov network 410 may infer that y is infected in the same day.

Figure 5:
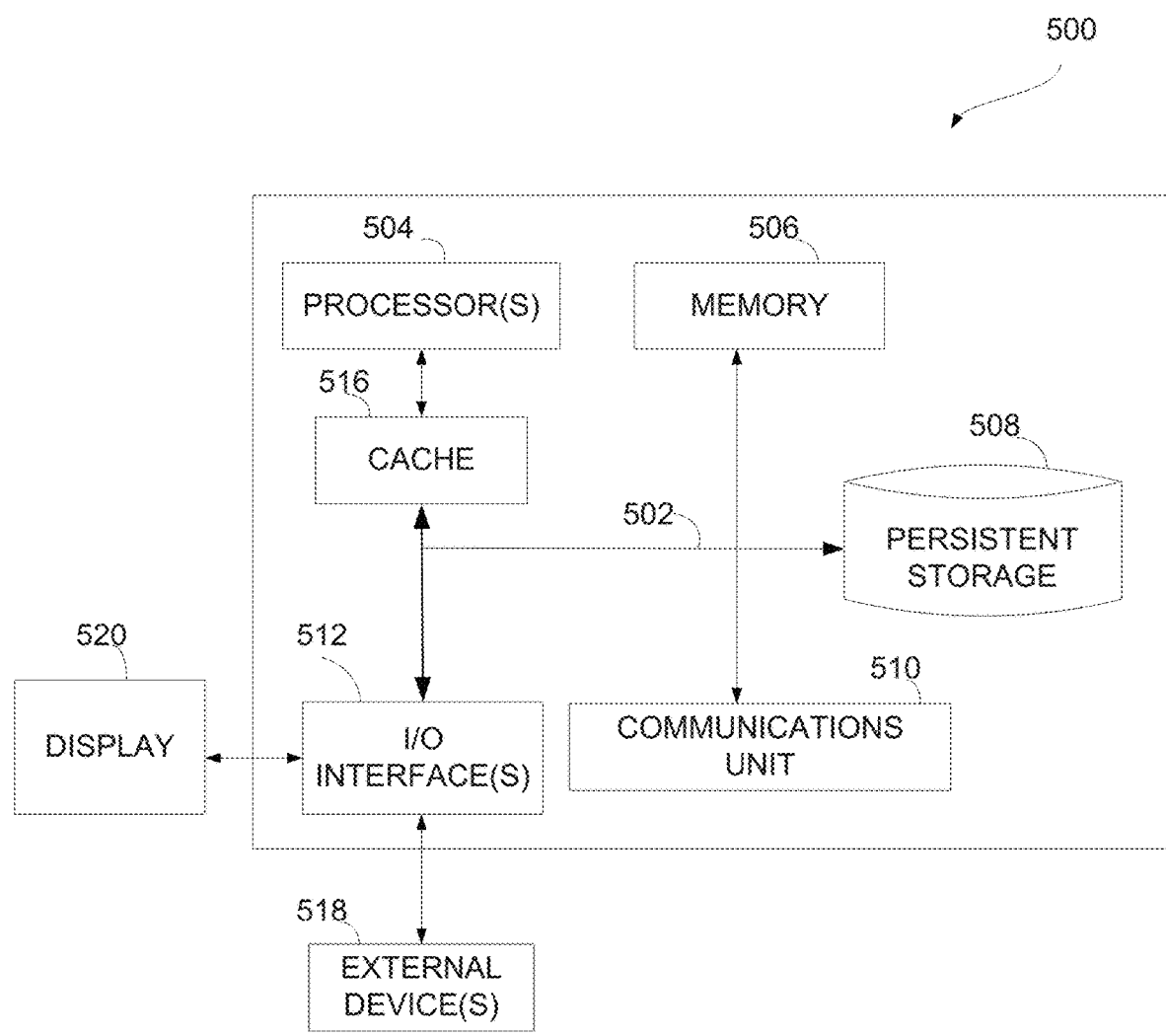
FIG. 5 is a block diagram of components of the computing device of FIG. 1, in accordance with an embodiment of the present disclosure.

FIG. 5 depicts a block diagram 500 of components of computing device 102 in accordance with an illustrative embodiment of the present disclosure. It should be appreciated that FIG. 5 provides only an illustration of one implementation and does not imply any limitations with regard to the environments in which different embodiments may be implemented. Many modifications to the depicted environment may be made.

Computing device 102 may include communications fabric 502, which provides communications between cache 516, memory 506, persistent storage 508, communications unit 510, and input/output (I/O) interface(s) 512. Communications fabric 502 can be implemented with any architecture designed for passing data and/or control information between processors (such as microprocessors, communications and network processors, etc.), system memory, peripheral devices, and any other hardware components within a system. For example, communications fabric 502 can be implemented with one or more buses or a crossbar switch.

Memory 506 and persistent storage 508 are computer readable storage media. In this embodiment, memory 506 includes random access memory (RAM). In general, memory 506 can include any suitable volatile or non-volatile computer readable storage media. Cache 516 is a fast memory that enhances the performance of computer processor(s) 504 by holding recently accessed data, and data near accessed data, from memory 506.

Safe route planning module 110 may be stored in persistent storage 508 and in memory 506 for execution by one or more of the respective computer processors 504 via cache 516. In an embodiment, persistent storage 508 includes a magnetic hard disk drive. Alternatively, or in addition to a magnetic hard disk drive, persistent storage 508 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 508 may also be removable. For example, a removable hard drive may be used for persistent storage 508. Other examples include optical and magnetic disks, thumb drives, and smart cards that are inserted into a drive for transfer onto another computer readable storage medium that is also part of persistent storage 508.

Communications unit 510, in these examples, provides for communications with other data processing systems or devices. In these examples, communications unit 510 includes one or more network interface cards. Communications unit 510 may provide communications through the use of either or both physical and wireless communications links. Safe route planning module 110 may be downloaded to persistent storage 508 through communications unit 510.

I/O interface(s) 512 allows for input and output of data with other devices that may be connected to computing device 102. For example, I/O interface 512 may provide a connection to external devices 518 such as a keyboard, keypad, a touch screen, and/or some other suitable input device. External devices 518 can also include portable computer readable storage media such as, for example, thumb drives, portable optical or magnetic disks, and memory cards. Software and data used to practice embodiments of the present invention, e.g., safe route planning module 110 can be stored on such portable computer readable storage media and can be loaded onto persistent storage 508 via I/O interface(s) 512. I/O interface(s) 512 also connect to display 520.

Display 520 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Python, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A computer-implemented method comprising:
    generating, by one or more processors, a contact graph for a user in a group of users in an area, based on a pre-defined distance measurement between the user and another user in a same timestamp during a pre-defined time period;
    building, by one or more processors, a profile for the user based on the contact graph, the profile including a probability model corresponding to the contact graph to estimate an infection probability for the user;
    calculating, by one or more processors, an initial route for the user from a first location to a second location in the area;
    analyzing, by one or more processors, an infection risk for the user based on the profile and other users within a pre-defined distance to the user in the initial route; and
    updating, by one or more processors, the initial route based on the analysis to minimize the risk to be infected.

2. The computer-implemented method of claim 1, wherein generating the contact graph comprises measuring a distance between the user and another user using a global positioning system.

3. The computer-implemented method of claim 1, wherein building the profile comprises generating a dataset based on position data collected from a global positioning system and medical data available from the group of users.

4. The computer-implemented method of claim 1, wherein calculating the initial route comprises using an algorithm to calculate and generate the shortest route as the initial route.

5. The computer-implemented method of claim 1, wherein the probability model is a Markov network with a same structure based on the contact graph.

6. The computer-implemented method of claim 5, wherein analyzing the infection risk of the user comprises using the Markov network to estimate the infection risk based on a pre-determined threshold.

7. The computer-implemented method of claim 1, wherein analyzing the infection risk for the user comprises analyzing multiple routes within the area and identifying users who share zones with an infected user.

8. A computer program product comprising:
    one or more computer readable storage media, and program instructions collectively stored on the one or more computer readable storage media, the program instructions comprising:
    program instructions to generate a contact graph for a user in a group of users in an area, based on a pre-defined distance measurement between the user and another user in a same timestamp during a pre-defined time period;
    program instructions to build a profile for the user based on the contact graph, the profile including a probability model corresponding to the contact graph to estimate an infection probability for the user;
    program instructions to calculate an initial route for the user from a first location to a second location in the area;
    program instructions to analyze an infection risk for the user based on the profile and other users within a pre-defined distance to the user in the initial route; and
    program instructions to update the initial route based on the analysis to minimize the risk to be infected.

9. The computer program product of claim 8, wherein program instructions to generate the contact graph comprise program instructions to measure a distance between the user and another user using a global positioning system.

10. The computer program product of claim 8, wherein program instructions to build the profile comprise program instructions to generate a dataset based on position data collected from a global positioning system and medical data available from the group of users.

11. The computer program product of claim 8, wherein program instructions to calculate the initial route comprise program instructions to use an algorithm to calculate and generate the shortest route as the initial route.

12. The computer program product of claim 8, wherein the probability model is a Markov network with a same structure based on the contact graph.

13. The computer program product of claim 12, wherein program instructions to analyze the infection risk of the user comprise program instructions to use the Markov network to estimate the infection risk based on a pre-determined threshold.

14. The computer program product of claim 8, wherein program instructions to analyze the infection risk for the user comprise program instructions to analyze multiple routes within the area and identifying users who share zones with an infected user.

15. A computer system comprising:
    one or more computer processors, one or more computer readable storage media, and program instructions stored on the one or more computer readable storage media for execution by at least one of the one or more computer processors, the program instructions comprising:

program instructions to generate a contact graph for a user in a group of users in an area, based on a pre-defined distance measurement between the user and another user in a same timestamp during a pre-defined time period;

program instructions to build a profile for the user based on the contact graph, the profile including a probability model corresponding to the contact graph to estimate an infection probability for the user;

program instructions to calculate an initial route for the user from a first location to a second location in the area;

program instructions to analyze an infection risk for the user based on the profile and other users within a pre-defined distance to the user in the initial route; and program instructions to update the initial route based on the analysis to minimize the risk to be infected.

16. The computer system of claim 15, wherein program instructions to generate the contact graph comprise program instructions to measure a distance between the user and another user using a global positioning system.

17. The computer system of claim 15, wherein program instructions to build the profile comprise program instructions to generate a dataset based on position data collected from a global positioning system and medical data available from the group of users.

18. The computer system of claim 15, wherein program instructions to calculate the initial route comprise program instructions to use an algorithm to calculate and generate the shortest route as the initial route.

19. The computer system of claim 15, wherein the probability model is a Markov network with a same structure based on the contact graph.

20. The computer system of claim 15, wherein program instructions to analyze the infection risk for the user comprise program instructions to analyze multiple routes within the area and identifying users who share zones with an infected user.

* * * * *